United States Patent [19]

Jonas et al.

[11] 3,980,797
[45] Sept. 14, 1976

[54] HEXAHYDRO-DIAZEPINO-INDOLE DERIVATIVES

[75] Inventors: Rochus Jonas; Helmut Müller-Calgan; Hans-Jochen Schliep, all of Darmstadt, Germany

[73] Assignee: Merck Patent Gesellschaft mit beschrankter Haftung, Darmstadt, Germany

[22] Filed: June 13, 1975

[21] Appl. No.: 586,808

[30] Foreign Application Priority Data
June 14, 1974 Germany............................ 2428691

[52] U.S. Cl........................ 424/274; 260/239.3 T; 260/326.11 R; 260/326.31; 260/326.5 B; 260/326.9
[51] Int. Cl.²................................... C07D 487/04
[58] Field of Search............... 260/326.5 B, 326.31, 260/326.9, 239.3 T; 424/274

[56] References Cited
UNITED STATES PATENTS
3,867,374  2/1975  Reynolds et al................ 260/239.3

*Primary Examiner*—Nicholas S. Rizzo
*Assistant Examiner*—Mary C. Vaughn
*Attorney, Agent, or Firm*—Millen, Raptes & White

[57] ABSTRACT

Hexahydro-diazepino-indoles of the formula

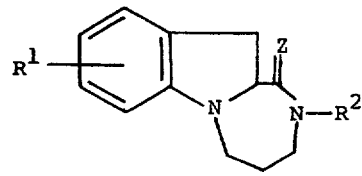

wherein $R^1$ is H, F, Cl, $CF_3$, alkyl or alkoxy each of 1 to 3 carbon atoms; $R^2$ is H, alkyl or cycloalkyl or alkenyl each of up to 6 carbon atoms, or alkyl of up to 6 carbon atoms substituted by oxo oxygen and/or amino or alkylated amino of 2 to 6 carbon atoms and/or aryl of 6 to 8 carbon atoms; and Z is O or (H,H), and physiologically acceptable acid addition salts thereof, possess CNS depressant activity.

32 Claims, No Drawings

HEXAHYDRO-DIAZEPINO-INDOLE DERIVATIVES

BACKGROUND OF THE INVENTION

This invention relates to new hexahydro-diazepinoindole derivatives.

SUMMARY OF THE INVENTION

In a composition aspect, this invention relates to novel hexahydro-diazepinoindoles of the general Formula I

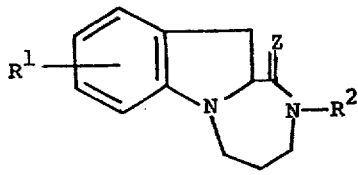

wherein $R^1$ is H, F, Cl, $CF_3$, alkyl or alkoxy each of 1 to 3 carbon atoms; $R^2$ is H, alkyl or cycloalkyl or alkenyl each of up to 6 carbon atoms, or alkyl of up to 6 carbon atoms substituted by oxo oxygen and/or amino or alkylated amino of 2 to 6 carbon atoms and/or aryl of 6 to 8 carbon atoms; and Z is O or (H,H), and physiologically acceptable acid addition salts thereof.

In another composition aspect, this invention relates to pharmaceutical compositions comprising an effective unit dosage amount of a compound of this invention.

In process aspects, this invention relates to methods for the production and use of the compounds of this invention.

DETAILED DISCUSSION

In Formula I, $R^1$ is preferably H or Cl and also F or methyl; additionally, $CF_3$, ethyl or methoxy; and finally also n-propyl, isopropyl, ethoxy, n-propoxy or isopropoxy.

When $R^2$ is alkyl or alkenyl, the groups preferably are of up to 4 carbon atoms and the cycloalkyl groups preferably are of 3 to 6 carbon atoms. Specifically, alkyl is preferably methyl or ethyl, also n-propyl, isopropyl, n-butyl or isobutyl, and also, for example, sec.-butyl, tert.-butyl, n-pentyl, isoamyl, n-hexyl and isohexyl. Cycloalkyl is preferably cyclopropyl, cyclobutyl, cyclopentyl or cyclohexyl, and also, for example, 2- or 3-methylcyclopentyl. Alkenyl is preferably vinyl, allyl, propenyl, isopropenyl, 2-buten-1-yl or 3-buten-1-yl. In the $R^2$ alkyl groups, two hydrogen atoms can be replaced by an oxygen atom. $R^2$ can, therefore, also be alkanoyl (1-oxo-alkyl), for example, formyl, acetyl, propionyl, butyryl, isobutyryl, valeryl, isovaleryl, trimethylacetyl, methylethylacetyl, n-caproyl, isocaproyl, tert.-butylacetyl and diethylacetyl. It is also possible for the oxo group in the radical $R^2$ to be in a position other than the 1-position and therefore not to be adjacent to the ring nitrogen atom and, accordingly, to be ketonic or aldehydic. Examples of such oxoalkyl groups are 2-oxoethyl (formylmethyl), 2- or 3-oxopropyl, 2-, 3- or 4-oxobutyl, 2-, 3-, 4- or 5-oxopentyl, or 2-, 3-, 4-, 5- or 6-oxohexyl. $R^2$ can also be alkyl substituted by amino or by alkylated amino of 2 to 6 carbon atoms, for example, 2-aminoethyl, 2- or 3-aminopropyl, 2-, 3- or 4-aminobutyl, 2-, 3-, 4- or 5-aminopentyl, 2-, 3-, 4-, 5- or 6-aminohexyl, 2-methylaminoethyl, 2- or 3-methylaminopropyl, 2-, 3- or 4-methylaminobutyl, dimethylaminomethyl, 2-dimethylaminoethyl, 2-methylethylaminoethyl, 2-diethylaminoethyl, 2-di-n-propylaminoethyl, 2-diisopropylaminoethyl, 2- or 3-dimethylaminopropyl, 2- or 3-diethylaminopropyl, 2- or 3-di-n-propylaminopropyl, 2- or 3-diisopropylaminopropyl, 2-, 3- or 4-dimethylaminobutyl, 2-, 3- or 4-diethylaminobutyl. $R^2$ can also be alkyl substituted by aryl of 6 to 8 carbon atoms, for example, benzyl, p-methylbenzyl, p-ethylbenzyl, 1- or 2-phenylethyl, 1-, 2- or 3-phenylpropyl, 1-, 2-, 3- or 4-phenylbutyl. $R^2$ can also be alkyl which is substituted both by one each of oxo oxygen, amino or alkylated amino of 2 to 6 carbon atoms or aryl, or any combination of two thereof or all three thereof. Accordingly, $R^2$ can be, for example, aminoacetyl, dimethylaminoacetyl, diethylaminoacetyl, 2- or 3-aminopropionyl, 2- or 3-dimethylaminopropionyl, phenylacetyl, 2- or 3-phenylpropionyl and p-dimethylaminophenylacetyl.

Z is preferably (H,H).

Accordingly, the invention relates particularly to those compounds of Formula I and their acid addition salts in which at least one of $R^1$, $R^2$ and Z has one of the preferred meanings specified above. Some of these preferred groups of compounds can be expressed by means of the partial formulae Ia to In which otherwise correspond to Formula I wherein:

Ia $R^1$ is H, F, Cl, $CF_3$, $CH_3$, $C_2H_5$ or $CH_3O$;

Ib $R^1$ is H, F, Cl or $CH_3$;

Ic $R^1$ is H or Cl;

Id $R^1$ is H;

Ie $R^2$ is H, alkyl or alkenyl each of up to 4 carbon atoms, cycloalkyl of 3 to 6 carbon atoms, alkanoyl of 1 to 4 carbon atoms, oxoalkyl of 3 or 4 carbon atoms, dialkylaminoalkyl or dialkylaminoalkanoyl each of a total of 4 to 7 carbon atoms, or arylalkyl of 7 to 10 carbon atoms;

If $R^2$ is H, $CH_3$, $C_2H_5$, cyclopropyl, cyclohexyl, allyl, alkanoyl having 1 to 4 carbon atoms, 3-oxobutyl, 3-dimethylaminopropyl, dimethylaminoacetyl, benzyl or p-methylbenzyl;

Ig $R^2$ is H, $CH_3$, $C_2H_5$ or 3-oxobutyl;

Ih $R^2$ is H;

Ii Z is (H,H);

Ij $R^1$ is H, F, Cl or $CH_3$ and $R^2$ is H, $CH_3$, $C_2H_5$, cyclopropyl, cyclohexyl, allyl, alkanoyl of 1 to 4 carbon atoms, 3-oxobutyl, 3-dimethylaminopropyl, dimethylaminoacetyl, benzyl or p-methylbenzyl;

Ik $R^1$ is H, F, Cl or $CH_3$ and $R^2$ is H, $CH_3$, $C_2H_5$ or 3-oxobutyl;

Il $R^1$ is H or Cl and $R^2$ is H, $CH_3$, $C_2H_5$ or 3-oxobutyl;

Im $R^1$ is H or 8—Cl and $R^2$ is H, $CH_3$, $C_2H_5$ or 3-oxobutyl;

In $R^1$ is H or 8—Cl, $R^2$ is H and Z is (H,H).

In a process aspect, this invention relates to a process for the preparation of hexahydro-diazepino-indole derivatives of Formula I and their physiologically acceptable acid addition salts wherein a compound of the general formula Y–$R^2$ (II) wherein Y is

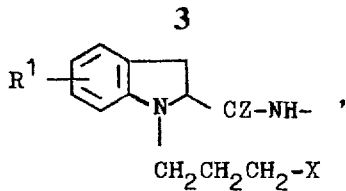

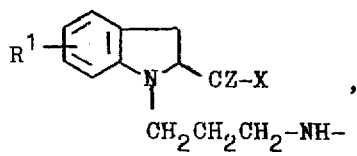

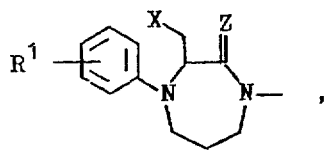

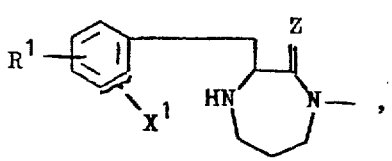

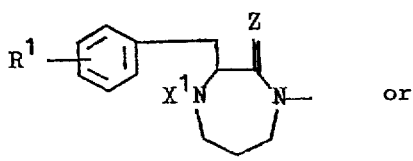

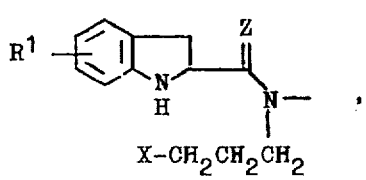

X is OH, functionally modified OH, Cl, Br, I, NH₂ or functionally modified NH₂, and X¹ is Cl or Br and R¹, R² and Z have the values given above, is treated with a cyclizing agent; or a compound otherwise corresponding to Formula I, but which contains, additionally or instead of H atoms, at least one reducible group and/or C—C and/or C–N multiple bonds, is treated with a reducing agent; and, optionally, a resulting compound of Formula I is converted into another compound of Formula I by treatment with a reducing, alkylating or acylating agent, and/or a resulting base of Formula I is converted into a physiologically acceptable acid addition salt by treatment with an acid, and/or a resulting acid addition salt is converted into the free base of Formula I by treatment with a base.

The specified preparation of the compounds of Formula I is carried out by methods which are in themselves known, such as are described in the literature (for example, in the standard works such as Houben-Weyl, Methoden der organischen Chemie ("Methods of Organic Chemistry"), Georg Thieme Verlag, Stuttgart), and in particular, under the reaction conditions which are known and suitable for the reactions mentioned.

The starting materials for the preparation of the compounds of Formula I can, if desired, also be formed in situ, in such a way that they are not isolated from the reaction mixture, but are at once reacted further to give a compound of Formula I.

More specifically, compounds of general Formulae IIa to IIf which are listed below are suitable for preparing the compounds of Formula I by cyclization:

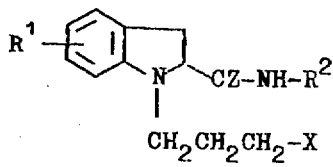

IIa

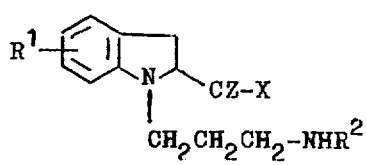

IIb

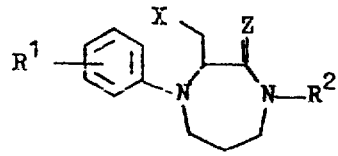

IIc

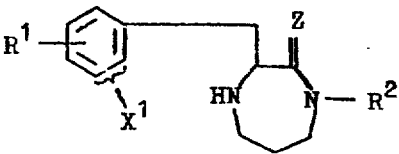

IId

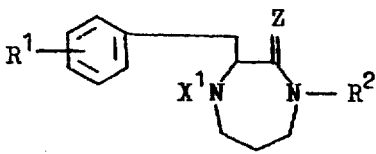

IIe

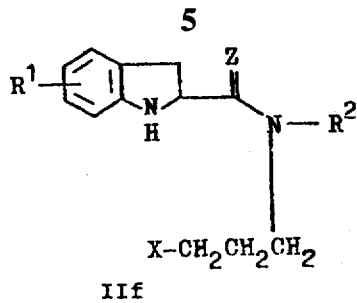

IIf wherein $R^1$, $R^2$, X, $X^1$ and Z have the values given above.

The indoline derivatives IIa, IIb and IIf are preferred for the cyclization.

In Formulae IIa to IIf, X is preferably Cl or Br. Besides free OH or I, X can, however, also be esterified OH, particularly reactively esterified OH, for example, alkylsulfonyloxy, having, in particular, 1 to 6 carbon atoms (for example, methanesulfonyloxy), arylsulfonyloxy having, in particular, 6 to 10 carbon atoms (for example, benzenesulfonyloxy, p-toluenesulfonyloxy or 1- or 2-naphthalenesulfonyloxy) or acyloxy, particularly alkanoyloxy, preferably of 1 to 7 carbon atoms (for example, acetoxy or heptanoyloxy) or benzoyloxy, and also an ether group which can be readily cleaved, e.g., tetrahydropyranyl-2-oxy. In addition, X can be a free or functionally modified amino group, for example, an acylated amino group, particularly alkanoylamino, preferably of 1 to 7 carbon atoms (for example, acetylamino or propionylamino) or benzoylamino. $X^1$ in Formula IId is in the o- or m-position to the hexahydrodiazepyl-methyl and the round bracket in Formula IId is intended to express this fact.

The starting materials of Formula II have not yet been described in the literature but can be prepared by methods which are in themselves known. For example, the indoline derivatives of Formulae IIa and IIb are obtained by reacting the corresponding indolines which are unsubstituted in the 1-position with acrylic acid or one of its derivatives, for example an acrylic acid alkyl ester or acrylonitrile, and subsequently converting the carboxyl, carbalkoxy or cyano group by reductive means into the group —$CH_2X$ or —$CH_2NHR^2$. The hexahydrodiazepines of Formula IIc can be obtained, for example, from aniline derivatives of the formula $R^1$—$C_6H_4$—NH—$(CH_2)_3NH$-$R^2$ and compounds of the formula X—$CH_2$—CHX—CZ—X, the groups X in the last-mentioned compounds preferably being different from each other. The hexahydrodiazepines of Formula IId can be obtained, for example, by reacting the diamines $H_2N$—$(CH_2)_3$—NH-$R^2$ with compounds of the formula $R^1X^1C_6H_3$—$CH_2$—CHX—CZ-X. The 1-chloro-hexahydrodiazepines or 1-bromo-hexahydrodiazepines of Formula IIe are preferably prepared by reacting diamines of the formula $H_2N$-$(CH_2)_3$—NH—$R^2$ with compounds of the formula $R^1$—$C_6H_4$—$CH_2$—CHX—CZ—X and subsequent N-halogenation. The indolines of Formula IIf are accessible by reacting an indoline which is substituted in the 2-position by the group -CZ-X, with a compound of the formula X—$(CH_2)_3$—NH—$R^2$, it being possible to limit undesired side-reactions to a minimum by appropriate choice of values for X in the individual starting materials.

The cyclization of the compounds of Formula II is carried out, as a rule, in the presence of a basic or acid catalyst and in the presence or absence of an additional inert solvent, at temperatures between about −20° and +300°.

The selection of the preferred catalysts depends essentially on the constitution of the starting material and of the compound HX or $HX^1$ which is to be split off. Examples of suitable bases are alkali metal hydroxides or alkaline earth metal hydroxides (for example, NaOH, KOH, Ba(OH)$_2$ or Ca(OH)$_2$), alkali metal carbonates or alkaline earth metal carbonates (for example $Na_2CO_3$ or $K_2CO_3$), alkali metal bicarbonates or alkaline earth metal bicarbonates (for example NaHCO$_3$ or KHCO$_3$), alkali metal hydrides or alkaline earth metal hydrides (for example, NaH or KH), alkali metal amides or alkaline earth metal amides (for example, NaNH$_2$ or KNH$_2$) or alkali metal alcoholates or alkaline earth metal alcoholates (for example, sodium methylate or potassium methylate, sodium ethylate or potassium ethylate, or potassium tert.-butylate) and also the alkali metal salts of weak acids (for example, sodium acetate), and also ammonia and primary, secondary and particularly, tertiary amines (for example, triethylamine, dimethylaniline and pyridine) and quaternary bases (for example, benzyl-trimethylammonium hydroxide). Examples of suitable acids are hydrogen halide acids, such as HF, HCl of HBr, sulfuric acid, phosphoric acid or polyphosphoric acid, as well as Lewis acids, such as AlCl$_3$, AlCl$_2$·HSO$_4$, AlBr$_3$, BF$_3$, ZnCl$_2$, GaCl$_3$ and GaBr$_3$. The last-mentioned acids and Lewis acids are especially suitable for the cyclization of compounds of Formula IIc, which is carried out by Friedel-Crafts alkylation. The compounds of Formula IId are advantageously cyclized by the action of strongly basic organo-alkali metal compounds (for example, phenyl-lithium or naphthylsodium), it being possible to add diethylamine or lithium piperidide. The corresponding arine is formed as an intermediate. The cyclization of the compounds of Formula IIe is preferably carried out in concentrated sulfuric acid, it being possible for iron-II salts, such as iron-II sulfate, copper-I chloride or sodium sulfate to be present as catalysts.

Particularly suitable inert solvents for the cyclization of compounds of Formulae IIa, IIb and IIf are alcohols, such as methanol, ethanol, isopropanol and n-butanol; ethers, such as diethyl ether, diisopropyl ether, tetrahydrofuran (THF), and dioxan; glycol ethers, such as ethylene glycol monomethyl or monoethyl ether (methylglycol or ethylglycol), ethylene glycol dimethyl ether (diglyme); ketones, such as acetone; hydrocarbons, such as benzene, toluene, xylene, petroleum ether and hexane; chlorinated hydrocarbons, such as methylene chloride, chloroform and trichloroethylene; amides, such as dimethylformamide (DMF); nitriles, such as acetonitrile; nitro compounds, such as nitromethane and nitrobenzene; and carbon disulfide. Mixtures of water with one of the alcohols mentioned, for example, 60% ethanol, and also mixtures of water with acetone or dioxan, are also suitable for the cyclization of compounds of Formulae IIa, IIb and IIf. The typical solvents which are suitable for Friedel-Crafts alkylations, such as petroleum ether, nitrobenzene and carbon disulfide are preferred for the cyclization of compounds of Formula IIc. These compounds can also by cyclized by the action of tertiary amines in high-boiling alcohols, such as cyclohexanol. The cyclization of the compounds of Formula IId is carried out particularly advantageously in one of the ethers mentioned. The cyclization of compounds of Formulae IIa, IIb and IIf is carried out particularly advantageously at temperatures from 20° to 200°, preferably from 50° to 130°, the cyclization of the compounds of Formula IIc is carried out particularly advantageously from about 0° to 150°, that of the compounds of Formula IId from about 0° to about 120°, and that of the compounds of Formula IIe at about −20° to about +100°.

The hexahydro-diazepino-indole derivatives of Formula I can also be obtained by reduction of corresponding compounds which contain, additionally or instead of H atoms, at least one reducible group and/or C-C and/or C-N multiple bond, preferably at temperatures between about −80° and +250°, in the presence of at least one inert solvent.

Reducible (replaceable by hydrogen) groups are particularly oxygen in a carbonyl group and also sulfur in a thiocarbonyl group or hydroxyl. The multiple bonds which are optionally present additionally are preferably double bonds, which can be in the 1(2)-, 2(3)-, 3(4)-, 4(5)-, 1(11a)- and/or 11(11a)-position. Such additional reducible groups are preferably in the 1-, 3-, 4-, 5- and/or 11-position. Accordingly, suitable starting materials for the reduction are preferably compounds of the general Formula IV

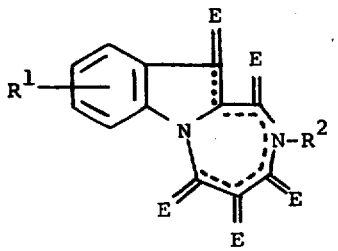

IV wherein the groups E are in each case O, S, (H,OH) or (H,H), $R^1$ and $R^2$ have the values given above and one or more additional C—C and/or C-N multiple bonds can be present in the positions marked by dots, but at least one of the groups E must be different from (H,H) or at least one additional multiple bond must be present.

In addition, chlorine, bromine or iodine atoms, oxygen in a N-oxide group, or mercapto or amino groups can be replaced by hydrogen. Among the compounds of Formula IV, preferred are those in which one or two of the E groups is an oxygen atom and the remainder are (H,H), the carbonyl groups being preferably located in the 3-position and/or the 5-position. A further preferred group of compounds of Formula IV, comprises indole derivatives which have an additional double bond in the 11(11a)-position with all E groups being hydrogen. These indole derivatives are, in part, known.

The starting materials of Formula IV can be obtained by methods which are in themselves known, for example, by reacting appropriate indoline derivatives which are unsubstituted in the 1-position and which carry the group —CE—NHR² in the 2-position, with compounds of the formula X—CE—CE—CE—X (wherein the E groups are, as a rule, different one from another; for example, reactive derivatives of 3-bromopropionic acid or of malonic acid) or with acrylic acid derivatives.

Catalytic hydrogenation or complex metal hydrides are preferably used for the reduction. It is, however, also possible to use other customary reducing agents, for example, metals in conjunction with acids or bases.

Examples of suitable catalysts for catalytic hydrogenations are nobel metal, nickel or cobalt catalysts, and also mixed catalysts such as copper-chromium oxide. Possible noble metals are primarily platinum and palladium, which can be present on supports (for example charcoal, calcium carbonate or strontium carbonate), as oxides or in a finely divided form. Nickel and cobalt catalysts are preferably employed as Raney metals. Hydrogenation can be carried out at pressures from about 1 to 100 atmospheres and at temperatures from about −80° to +150°, preferably 20° to 100°. The reaction can be carried out in an acid, neutral or basic range, preferably in the presence of one of the inert solvents already mentioned above or in the presence of a carboxylic acid, such as acetic acid, or an ester, such as ethyl acetate.

It is also possible to use complex metal hydrides, such as $LiAlH_4$ or $NaBH_4$ as well as diborane as reducing agents, with the optional addition of a catalyst, such as $BF_3$, $AlCl_3$ or LiBr. For example, the lactams are advantageously reduced by means of $LiAlH_4$. Suitable solvents for this purpose are, in particular, the ethers mentioned, however, for a reduction by means of $NaBH_4$, alcohols such as methanol or ethanol are suitable. Reduction is preferably carried out at temperatures from about −80° to +150°, particularly 20° to 120°.

Keto groups can also be reduced to $CH_2$ groups by the methods of Clemmensen (using zinc and hydrochloric acid) or Wolff-Kishner (using hydrazine). A double bond in the 11(11a)-position can be advantageously reduced by means of tin/hydrochloric acid, preferably at about 0°.

If desired, a resulting compound of Formula I can be converted into another compound of Formula I by reduction, alkylation or acylation.

For example, it is possible to reduce an oxo group in the 1-position (Z equals 0) or in a 2-acyl group ($R^2$ = 1-oxoalkyl) to a $CH_2$ group, preferably using $LiAlH_4$ under the conditions indicated above. In addition, double bonds in a 2-alkenyl group ($R^2$ = alkenyl) can be hydrogenated or 2-benzyl groups ($R^2$ = benzyl or p-methylbenzyl) can be removed by hydrogenolysis, preferably using hydrogen with a noble metal catalyst at room temperature and normal pressure (as indicated above). N-benzyl groups can also be split off with sodium in liquid ammonia.

In addition, it is possible to introduce another $R^2$ group into a compound of Formula I ($R^2$ = H) by alkylation or acylation, the term "alkylation" being used in the broadest sence, includes cycloalkylation, alkenylation, oxoalkylation, aminoalkylation and aralkylation. Examples of alkylating agents are preferably alkyl halides, such as methyl iodide, ethyl bromide and isopropyl chloride, and also, for example, cyclopropyl chloride, bromide or iodide, cyclobutyl chloride, bromide or iodide, cyclopentyl chloride, bromide or iodide, and cyclohexyl chloride, bromide or iodide, allyl chloride, bromide or iodide, or propenyl chloride, bromide or iodide, dialkylaminoalkyl halides, such as 2-dimethylaminoethyl chloride, 3-dimethylaminopropyl bromide and the like, or benzyl chloride, bromide, or iodide; alkyl esters of inorganic acids, such as dimethyl sulfate, or of organic sulfonic acids, such as methyl p-toluene-sulfonate; halogenoketones, such as chloroacetone and bromoacetone; or unsaturated ketones, such as methyl vinyl ketone. It is also possible to alkylate using aldehydes or ketones under reducing conditions, the corresponding aldehyde ammonia being formed as intermediate products. For example, a methyl group can be introduced using formaldehyde in the presence of formic acid. In addition, alkylation can be carried out by means of an alcohol of 1 to 6 carbon atoms, in the presence of Raney nickel. The alkylation is preferably carried out in the presence or absence of one of the inert solvents above mentioned at temperatures of about 0° to about 120°, preferably 40° to 100°, and one of the catalysts specified can be present, preferably a base, such as potassium tert.-butylate. A preferred solvent for the alkylation is DMF. The reactions with unsaturated ketones are preferably carried out in benzene at room temperature.

An acylation is preferably carried out by means of a halide (for example, chloride or bromide) or anhydride of the corresponding carboxylic acid, for example, acetic anhydride, isobutyryl bromide or dimethylaminoacetyl chloride. The addition of a base, such as pyridine or triethylamine, is possible, but not necessary. The acylation is preferably also carried out in the presence or absence of one of the inert solvents mentioned at temperatures of about 0° to about 160°, preferably about 100° to 150°.

A base of Formula I can be converted into the appropriate acid addition salt in the customary manner with acid. Suitable acids for this reaction are those which give physiologically acceptable salts, which include inorganic acids, for example, sulfuric acid, nitric acid, hydrogen halide acids, such as hydrochloric acid and hydrobromic acid, phosphoric acids, such as orthophosphoric acid, and also organic acids, particularly aliphatic, alicyclic, araliphatic, aromatic or heterocyclic, monobasic or polybasic carboxylic or sulfonic acids, such as formic acid, acetic acid, propionic acid, pivalic acid, diethylacetic acid, malonic acid, succinic acid, pimelic acid, fumaric acid, maleic acid, lactic acid, tartaric acid, malic acid, sulfamic acid, benzoic acid, salicylic acid, 2-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid or naphthalenemonosulfonic and -di-sulfonic acids.

The free bases of Formula I can, if desired, be liberated from their salts by treatment with strong bases, such as sodium hydroxide, potassium hydroxide, sodium carbonate or potassium carbonate.

The compounds of Formula I can have one or more centers of asymmetry. They can, therefore, when synthesized, be obtained as racemates or even in an optically active form, if optically active starting materials are used. If the compounds have two or more centers of asymmetry, they are generally produced in the synthesis as mixtures of racemates from which the individual racemates can be isolated in a pure form, for example, by recrystallization from inert solvents. If desired, resulting racemates can be separated into their optical antipodes mechanically or chemically by methods which are in themselves known. Preferably diastereomers are formed from the racemate by reaction with an optically active resolving agent. Examples of suitable resolving agents are optically active acids, such as tartaric acid, dibenzoyltartaric acid, diacetyltartaric acid, camphorsulfonic acids, mandelic acid, malic acid or lactic acid.

The novel compounds of this invention are well tolerated and possess valuable pharmacological properties, particularly effects on the central nervous system, and particularly they exhibit central nervous depressant effects, more specifically, effects which enhance narcosis which can be demonstrated, for example, on mice or rats in accordance with the method of Janssen et al. (Journal of Medicinal and Pharmaceutical Chemistry, Vol. 1, 1959, pp. 281–297). They are also active in the avoidance-inhibition test. (Compare Müller-Calgan et al., Arch. Pharmacol. Exptl. Pathol., Vol. 260, 1968, pp. 178–179.) In addition, the compounds have an anticataleptic effect on rats, which effect can be determined by inducing catalepsy in experimental animals by means of Tetrabenazin (administered intravenously), which catalepsy in antagonized by the compounds of this invention with which the animals have been pre-treated (subcutaneously). In addition, in lower doses, the compounds exhibit a temperature-rising effect. Tranquilizing, adrenolytic and muscle-relaxing effects are also found, which can be estabilshed by methods which are customary for this purpose. The effects mentioned can be determined, for example, on mice, rats and Rhesus monkeys.

The compounds of Formula I and their physiologically acceptable acid addition salts can, therefore, be used as medicaments and also as intermediate products for the preparation of other medicaments. For example, they can be dehydrogenated to give the corresponding 2,3,4,5-tetrahydro-1H-1,4-diazpino[1,2-a]indoles, which have blood pressure lowering activity.

The novel compounds of Formula I and their physiologically acceptable acid addition salts can be employed as medicaments in human or veterinary medicine mixed with solid, liquid and/or semi-liquid medicinal excipients. Excipient substances which can be used are organic or inorganic materials which are suitable for enteral, parenteral or topical application and which do not react with the new compounds, such as, for example, water, vegetable oils, polyethylene glycols, gelatine, lactose, starch, magnesium stearate, talc or petroleum jelly. Tablets, dragees, capsules syrups, elixirs or suppositories are suitable for enteral administration. Solutions, particularly oily or aqueous solutions, and also suspensions, emulsions or implants are, in particular, used for parenteral administration, while ointments, creams or powders are used for topical application. These preparations can be sterilized and/or treated with auxiliary materials, such as preservatives, stabilizers and/or wetting agents, salts for controlling the osmotic pressure, buffer substances or coloring, flavoring and/or aroma substances. If desired, they can also contain one or more other active compounds.

The compounds of this invention are preferably administered in dosages of about 1 to 500 mg., especially 5 to 50 mg., per dosage unit. The daily dosage is preferably about 0.02 to 10 mg/kg., of body weight. Oral administration is preferred.

Each of the compounds of Formula I mentioned in the following examples is particularly suitable for the production of such pharmaceutical preparations.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1 a. A mixture of 2.69 g. of 1-(3-bromopropyl)-2-aminomethylindoline (obtainable by reacting 2-acetamidomethylindoline with 1,3-dibromopropane and subsequently splitting off the acetyl group with HBr), 100 ml. of 60% aqueous ethanol and 1.4 g. of potassium carbonate is boiled for 12 hours. The alcohol is then distilled off and the aqueous phase is worked up in the customary manner with chloroform. This gives 2,3,4,5,11,11a-hexahydro-1H-1,4-diazepino[1,2-a]-indole. Hydrochloride m.p. 234°.

The following compounds are obtained analogously from the correspondingly substituted 1-(3-bromopropyl)-2-aminomethyl-indolines:

7-Fluoro-2,3,4,5,11,11a-hexahydro-1H-1,4-diazepino[1,2-a]-indole,
8-fluoro-2,3,4,5,11,11a-hexahydro-1H-1,4-diazepino[1,2-a]-indole,
9-fluoro-2,3,4,5,11,11a-hexahydro-1H-1,4-diazepino[1,2-a]-indole, hydrochloride, m.p. 202°,
10-fluoro-2,3,4,5,11,11a-hexahydro-1H-1,4-diazepino[1,2-a]-indole,
7-chloro-2,3,4,5,11,11a-hexahydro-1H-1,4-diazepino[1,2-a]-indole,
8-chloro-2,3,4,5,11,11a-hexahydro-1H-1,4-diazepino[1,2-a]-indole, hydrochloride, m.p. 226°,
9-chloro-2,3,4,5,11,11a-hexahydro-1H-1,4-diazepino[1,2-a]-indole, hydrochloride, m.p. 158°,
10-chloro-2,3,4,5,11,11a-hexahydro-1H-1,4-diazepino[1,2-a]-indole, hydrochloride, m.p. 258°,
7-trifluoromethyl-2,3,4,5,11,11a-hexahydro-1H-1,4-diazepino[1,2-a]indole,
8-trifluoromethyl-2,3,4,5,11,11a-hexahydro-1H-1,4-diazepino[1,2-a]indole,
9-trifluoromethyl-2,3,4,5,11,11a-hexahydro-1H-1,4-diazepino[1,2-a]indole,
10-trifluoromethyl-2,3,4,5,11,11-hexahydro-1H-1,4-diazepino[1,2-a]indole,
7-methyl-2,3,4,5,11,11a-hexahydro-1H-1,4-diazepino[1,2-a]-indole,
8-methyl-2,3,4,5,11,11a-hexahydro-1H-1,4-diazepino[1,2-a]-indole,
9-methyl-2,3,4,5,11,11a-hexahydro-1H-1,4,-diazepino[1,2-a]-indole, hydrochloride, m.p. 223°,
10-methyl-2,3,4,5,11,11a-hexahydro-1H-1,4-diazepino[1,2-a]-indole,
7-ethyl-2,3,4,5,11,11a-hexahydro-1H-1,4-diazepino[1,2-a]-indole,
8-ethyl2,3,4,5,11,11a-hexahydro-1H-1,4-diazepino[1,2-a]-indole,
9-ethyl-2,3,4,5,11,11a-hexahydro-1H-1,4-diazepino[1,2-a]-indole,
10-ethyl-2,3,4,5,11,11a-hexahydro-1H-1,4-diazepino-[1,2-a]indole,
7-n-propyl-2,3,4,5,11,11a-hexahydro-1H-1,4-diazepino[1,2-a]-indole,
8-n-propyl-2,3,4,5,11,11a-hexahydro-1H-1,4-diazepino-[1,2-a]indole
9-n-propyl-2,3,4,5,11,11a-hexahydro-1H-1,4-diazepino[1,2-a]-indole,
10-n-propyl-2,3,4,5,11,11a-hexahydro-1H-1,4-diazepino[1,2-a]indole,
7-isopropyl-2,3,4,5,11,11a-hexahydro-1H-1,4-diazepino[1,2-a]indole,
8-isopropyl-2,3,4,5,11,11a-hexahydro-1H-1,4-diazepino[1,2-a]indole,
9-isopropyl-2,3,4,5,11,11a-hexahydro-1H-1,4-diazepino[1,2-a]indole,
10-isopropyl-2,3,4,5,11,11a-hexahydro-1H-1,4-diazepino[1,2-a]indole,
7-methoxy-2,3,4,5,11,11a-hexahydro-1H-1,4-diazepino[1,2-a]-indole,
8-methoxy-2,3,4,5,11,11a-hexahydro-1H-1,4-diazepino[1,2-a]-indole,
9-methoxy-2,3,4,5,11,11a-hexahydro-1H-1,4-diazepino[1,2-a]-indole, hydrochloride, m.p. 240°,
10-methoxy-2,3,4,5,11,11a-hexahydro-1H-1,4-diazepino-[1,2-a]indole,
7-ethoxy-2,3,4,5,11,11a-hexahydro-1H-1,4-diazepino[1,2-a]-indole,
8-ethoxy-2,3,4,5,11,11a-hexahydro-1H-1,4-diazepino[1,2-a]-indole,
9-ethoxy-2,3,4,5,11,11a-hexahydro-1H-1,4-diazepino[1,2-a]-indole,
10-ethoxy-2,3,4,5,11,11a-hexahydro-1H-1,4-diazepino[1,2-a]-indole,
7-n-propoxy-2,3,4,5,11,11a-hexhydro-1H-1,4-diazepino-[1,2-a]indole,
8-n-propoxy-2,3,4,5,11,11a-hexahydro-1H-1,4-diazepino-[1,2-a]indole,
9-n-propoxy-2,3,4,5,11,11a-hexahydro-1H-1,4-diazepino-[1,2-a]indole,
10-n-propoxy-2,3,4,5,11,11a-hexahydro-1H-1,4-diazepino[1,2-a]indole,
7-isopropoxy-2,3,4,5,11,11a-hexahydro-1H-1,4-diazepino[1,2-a]indole,
8-isopropoxy-2,3,4,5,11,11a-hexahydro-1H-1,4-diazepino[1,2-a]indole,
9-isopropoxy-2,3,4,5,11,11a-hexahydro-1H-1,4-diazepino[1,2-a]indole and
10-isopropoxy-2,3,4,5,11,11a-hexahydro-1H-1,4-diazepino[1,2-a]indole.

b. 1.88 g of 2,3,4,5,11,11a-hexahydro-1H-1,4-diazepino-[1,2-a]indole in 20 ml of DMF are stirred for one hour at 20° with 1.48 g of K tert.-butylate, 1.1 g of ethyl bromide are added and the solution is stirred for a further 10 hours. 200 ml of water are then added and the mixture is extracted several times with ethyl acetate. After drying and evaporating the organic phase, 2-ethyl-2,3,4,5,11,11a-hexahydro-1H-1,4-diazepino[1,2-a]indole is obtained. Hydrochloride, m.p. 204°.

The following compounds are obtained using the coresponding halides (for example, methyl iodide, cyclohexyl bromide, allyl bromide, bromoacetone, benzyl chloride and the like):

2-Methyl-2,3,4,5,11,11a-hexahydro-1H-1,4-diazepino[1,2-a]-indole, hydrochloride, m.p. 237°,
2-n-propyl-2,3,4,5,11,11a-hexahydro-1H-1,4-diazepino[1,2-a]-indole,
2-isopropyl-2,3,4,5,11,11a-hexahydro-1H-1,4-diazepino-[1,2-a]indole,
2-n-butyl-2,3,4,5,11,11a-hexahydro-1H-1,4-diazepino[1,2-a]-indole,
2-isobutyl-2,3,4,5,11,11a-hexahydro-1H-1,4diazepino-[1,2-a]-indole,
2-sec.-butyl-2,3,4,5,11,11a-hexahydro-1H-1,4-diazepino-[1,2-a]indole,
2-tert.-butyl-2,3,4,5,11,11a-hexahydro-1H-1,4-diazepino-[1,2-a]indole, 2-n-pentyl-2,3,4,5,11,11a-hexahydro-1H-1,4-diazepino-[1,2-a]-indole, 2-n-hexyl-2,3,4,5,11,11a-hexahydro-1H-1,4-diazepino-[1,2-a]-indole, dihydrobromide, m.p. 214°, 2-cyclopropyl-2,3,4,5,11,11a-hexahydro-1H-1,4-diazepino-[1,2-a]indole, 2-cyclobutyl-2,3,4,5,11,11a-hexahydro-1H-1,4-diazepino-[1,2-a]indole, 2-cyclopentyl-2,3,4,5,11,11a-hexahydro-1H-1,4-diazepino-[1,2-a]indole, 2-cyclohexyl-2,3,4,5,11,11a-hexahydro-1H-1,4-diazepino-[1,2-a]indole, 2-allyl-2,3,4,5,11,11a-hexahydro-1H-1,4-diazepino-[1,2-a]-indole, hydrochloride, m.p. 211°, 2-(2-oxopropyl)-2,3,4,5,11,11a-hexahydro-1H-1,4-diazepino-[1,2-a]indole, 2-benzyl-2,3,4,5,11,11a-hexahydro-1H-1,4-diazepino-[1,2-a]-indole, 2-(2-phenylethyl)-2,3,4,5,11,11a-hexahydro-1H-1,4-diazepino-[1,2-a]indole, 2-p-methylbenzyl-2,3,4,5,11,11a-hexahydro-1H-1,4-diazepino-[1,2-a]indole, 2-(3-dimethylaminopropyl)-2,3,4,5,11,11a-hexahydro-1H-1,4-diazeppino[1,2-a]indole, dihydrobromide, m.p. 261°, 2-(3-dimethylaminopropyl)-8-chloro-2,3,4,5,11,11a-hexahydro-1H-1,4-diazepino[1,2-a]indole, dihydrochloride, m.p. 269°, and 2-(3-diethylaminopropyl)-2,3,4,5,11,11a-hexahydro-1,4-diazepino-[1,2-a]indole, dihydrobromide, m.p. 212.

c. 1.88 g of 2,3,4,5,11,11a-hexahydro-1H-1,4-diazepino[1,2-a]indole are boiled with 10 ml of acetic anhydride for 3 hours and the mixture is evaporated and worked up with water and ether to give 2-acetyl-2,3,4,5,11,11a-hexahydro-1H-1,4-diazepino[1,2-a]indole, hydrochloride, m.p. 211°.

The following compounds are obtained analogously using the corresponding acid anhydrides, acid chlorides or acid esters:

2-Propionyl-2,3,4,5,11,11a-hexahydro-1H-1,4-diazepino-[1,2-a]indole, 2-butyryl-2,3,4,5,11,11a-hexahydro-1H-1,4-diazepino[1,2-a]-indole, 2-isobutyryl-2,3,4,5,11,11a-hexahydro-1H-1,4-diazepino[1,2-a]indole, hydrochloride, m.p. 187°, 2-valeryl-2,3,4,5,11,11a-hexahydro-1H-1,4-diazepino[1,2-a]-indole, 2-caproyl-2,3,4,5,11,11a-hexahydro-1H-1,4-diazepino[1,2-a]-indole, 2-benzoyl-2,3,4,5,11,11a-hexahydro-1H-1,4-diazepino[1,2-a]-indole, 2-phenylacetyl-2,3,4,5,11,11a-hexahydro-1H-1,4-diazepino-[1,2-a]indole, 2-dimethylaminoacetyl-2,3,4,5,11,11a-hexahydro-1H-1,4-diazepino[1,2-a]indole, dihydrobromide, m.p. 230°, 2-diethylaminoacetyl-2,3,4,5,11,11a-hexahydro-1H-1,4-diazepino[1,2-a]indole and 2-(3-dimethylaminopropionyl)-2,3,4,5,11,11-hexahydro-1H-1,4-diazepino[1,2-a]indole.

d. A solution of 1.88 g of 2,3,4,5,11,11a-hexahydro-1H-1,4-diazepino[1,2-a]indole and 0.7 g of methyl vinyl ketone in 30 ml of benzene is allowed to stand overnight at 20°. The mixture is evaporated, the residue is dissolved in dilute hydrochloric acid and washed with chloroform, and the solution is made alkaline with sodium hydroxide solution and extracted with chloroform and the chloroform extract is evaporated to give 2-(3-oxobutyl)-2,3,4,5,11,11a-hexahydro-1H-1,4-diazepino[1,2-a]indole. Hydrochloride, m.p. 165°.

The following compounds are obtained analogously using methyl vinyl ketone:

2-(3-Oxobutyl)-7-fluoro-2,3,4,5,11,11a-hexahydro-1H-1,4-diazepino[1,2-a]indole, 2-(3-oxobutyl)-8-fluoro-2,3,4,5,11,11a-hexahydro-1H-1,4-diazepino[1,2-a]indole, 2-(3-oxobutyl)-9-fluoro-2,3,4,5,11,11a-hexahydro-1H-1,4-diazepino[1,2-a]indole, 2-(3-oxobutyl)-10-fluoro-2,3,4,5,11,11a-hexahydro-1H-1,4-diazepino[1,2-a]indole, 2-(3-oxobutyl)-7-chloro-2,3,4,5,11,11a-hexahydro-1H-1,4-diazepino[1,2-a]indole, 2-(3-oxobutyl)-8-chloro-2,3,4,5,11,11a-hexahydro-1H-1,4-diazepino[1,2-a]indole, hydrochloride, m.p. 167°, 2-(3-oxobutyl)-9-chloro-2,3,4,5,11,11a-hexahydro-1H-1,4-diazepino[1,2-a]indole, 2-(3-oxobutyl)-10-chloro-2,3,4,5,11,11a-hexahydro-1H-1,4-diazepino[1,2-a]indole, hydrochloride, m.p. 182°, 2-(3-oxobutyl)-7-trifluoromethyl-2,3,4,5,11,11a-hexahydro-1H-1,4-diazepino[1,2-a]indole, 2-(3-oxobutyl)-8-trifluoromethyl-2,3,4,5,11,11a-hexahydro-1H-1,4-diazepino[1,2-a]indole, 2-(3-oxobutyl)-9-trifluoromethyl-2,3,4,5,11,11a-hexahydro-1H-1,4-diazepino[1,2-a]indole, 2-(3-oxobutyl)-10-trifluoromethyl-2,3,4,5,11,11a-hexahydro-1H-1,4-diazepino[1,2-a]indole, 2-(3-oxobutyl)-7-methyl-2,3,4,5,11,11a-hexahydro-1H-1,4-diazepino[1,2-a]indole, 2-(3-oxobutyl)-8-methyl-2,3,4,5,11,11a-hexahydro-1H-1,4-diazepino[1,2-a]indole, 2-(3-oxobutyl)-9-methyl-2,3,4,5,11,11a-hexahydro-1H-1,4-diazepino[1,2-a]indole, 2-(3-oxobutyl)-10-methyl-2,3,4,5,11,11a-hexahydro-1H-1,4-diazepino[1,2-a]indole, 2-(3-oxobutyl)-7-methoxy-2,3,4,5,11,11a-hexahydro-1H-1,4-diazepino[1,2-a]indole, 2-(3-oxobutyl)-8-methoxy-2,3,4,5,11,11a-hexahydro-1H-1,4-diazepino[1,2-a]indole, 2-(3-oxobutyl)-9-methoxy-2,3,4,5,11,11a-hexahydro-1H-1,4-diazepino[1,2-a]indole and 2-(3-oxobutyl)-10-methoxy-2,3,4,5,11,11a-hexahydro-1H-1,4-diazepino[1,2-a]indole.

EXAMPLE 2 a. A solution of 2.9 g of 1-(3-acetamidopropyl)-indoline-2-carboxylic acid ethyl ester (obtainable by catalytic hydrogenation of 1-(2-cyanoethyl)-indoline-2-carboxylic acid ethyl ester in acetic anhydride) in 35 ml of xylene is treated with 1 g of sodium hydride (in the form of a 20% suspension in paraffin oil) and the mixture is boiled for 2 hours. The mixture is evaporated and worked up with water and chloroform to give 1-oxo-2,3,4,5,11,11a-hexahydro-1H-1,4-diazepino[1,2-a]indole, m.p. 159° (from isopropanol/ether).

The following compounds are obtained analogously from the correspondingly substituted 1-(3-acetamidopropyl)-indoline-2-carboxylic acid methyl or ethyl esters:

1-Oxo-7-fluoro-2,3,4,5,11,11a-hexahydro-1H-1,4-diazepino-[1,2-a]indole, 1-oxo-8-fluoro-2,3,4,5,11,11a-hexahydro-1H-1,4-diazepino-[1,2-a]indole, 1-oxo-9-fluoro-2,3,4,5,11,11a-hexahydro-1H-1,4-diazepino-[1,2-a]indole, m.p. 188°, 1-oxo-10-fluoro-2,3,4,5,11,11a-hexahydro-1H-1,4-diazepino-[1,2-a]indole, 1-oxo-7-chloro-2,3,4,5,11,11a-hexahydro-1H-1,4-diazepino-[1,2-a]indole, 1-oxo-8-chloro-2,3,4,5,11,11a-hexahydro-1H-1,4-diazepino-[1,2-a]indole, m.p. 174°, 1-oxo-9-chloro-2,3,4,5,11,11a-hexahydro-1H-1,4-diazepino-[1,2-a]indole, m.p. 180°, 1-oxo-10-chloro-2,3,4,5,11,11a-hexahydro-1H-1,4-diazepino-[1,2-a]indole, 1-oxo-7-trifluoromethyl-2,3,4,5,11,11a-hexahydro-1H-1,4-diazepino[1,2-a]indole, 1-oxo-8-trifluoromethyl-2,3,4,5,11,11a-hexahydro-1H-1,4-diazepino[1,2-a]indole, 1-oxo-9-trifluoromethyl-2,3,4,5,11,11a-hexahydro-1H-1,4-diazepino[1,2-a]indole, 1-oxo-10-trifluoromethyl-2,3,4,5,11,11a-hexahydro-1H-1,4-diazepino[1,2-a]indole, 1-oxo-7-methyl-2,3,4,5,11,11a-hexahydro-1H-1,4-diazepino-[1,2-a]indole, 1-oxo-8-methyl-2,3,4,5,11,11a-hexahydro-1H-1,4-diazepino-[1,2-a]indole, 1-oxo-9-methyl-2,3,4,5,11,11a-hexahydro-1H-1,4-diazepino-[1,2-a]indole, m.p. 154°, 1-oxo-10-methyl-2,3,4,5,11,11a-hexahydro-1H-1,4-diazepino-[1,2-a]indole, 1-oxo-7-methoxy-2,3,4,5,11,11a-hexahydro-1H-1,4-diazepino-[1,2-a]indole, 1-oxo-8-methoxy-2,3,4,5,11,11a-hexahydro-1H-1,4-diazepino-[1,2-a]indole, 1-oxo-9-methoxy-2,3,4,5,11,11a-hexahydro-1H-1,4-diazepino-[1,2-a]indole, m.p. 137°, and 1-oxo-10-methoxy-2,3,4,5,11,11a-hexahydro-1H-1,4-diazepino-[1,2-a]indole.

b. 1.5 g of potassium tert.-butylate are added to a solution of 2.02 g of 1-oxo-2,3,4,5,11,11a-hexahydro-1H-1,4-diazepino[1,2-a]indole in 45 ml of DMF and the mixture is stirred for 1 hour. A solution of 1.6 g of 3-dimethylaminopropyl chloride in 7 ml of DMF is then added and the mixture is stirred for 10 hours at 20°. It is then poured onto water, extracted several times with ethyl acetate and worked up in the customary manner. This gives 1-oxo-2-(3-dimethylaminopropyl)-2,3,4,5,11,11a-hexahydro-1H-1,4-diazepino[1,2-a]indole. Dihydrobromide, m.p. 197°.

The following compounds are obtained analogously, using the corresponding halides:

1-Oxo-2-methyl-2,3,4,5,11,11a-hexahydro-1H-1,4-diazepino-[1,2-a]indole, hydrobromide, m.p. 241°, 1-oxo-2-ethyl-2,3,4,5,11,11a-hexahydro-1H-1,4-diazepino-[1,2-a]indole, 1-oxo-2-n-propyl-2,3,4,5,11,11a-hexahydro-1H-1,4-diazepino-[1,2-a]indole, 1-oxo-2-isopropyl-2,3,4,5,11,11a-hexahydro-1H-1,4-diazepino-[1,2-a]indole, 1-oxo-2-n-butyl-2,3,4,5,11,11a-hexahydro-1H-1,4-diazepino-[1,2-a]indole, 1-oxo-2-isobutyl-2,3,4,5,11,11a-hexahydro-1H-1,4-diazepino-[1,2-a]indole, 1-oxo-2-sec.-butyl-2,3,4,5,11,11a-hexahydro-1H-1,4-diazepino-[1,2-a]indole, 1-oxo-2-tert.-butyl-2,3,4,5,11,11a-hexahydro-1H-1,4-diazepino[1,2-a]indole, 1-oxo-2-n-pentyl-2,3,4,5,11,11a-hexahydro-1H-1,4-diazepino-[1,2-a]indole, 1-oxo-2-n-hexyl-2,3,4,5,11,11a-hexahydro-1H-1,4-diazepino-[1,2-a]indole, 1-oxo-2-cyclopropyl-2,3,4,5,11,11a-hexahydro-1H-1,4-diazepino[1,2-a]indole, 1-oxo-2-cyclobutyl-2,3,4,5,11,11a-hexahdyro-1H-1,4-diazepino[1,2-a]indole, 1-oxo-2-cyclopentyl-2,3,4,5,11,11a-hexahydro-1H-1,4-diazepino[1,2-a]indole, 1-oxo-2-cyclohexyl-2,3,4,5,11,11a-hexahydro-1H-1,4-diazepino[1,2-a]indole, 1-oxo-2-allyl-2,3,4,5,11,11a-hexahydro-1H-1,4-diazepino-[1,2-a]indole, m.p. 170°, 1-oxo-2-(2-oxopropyl)-2,3,4,5,11,11a-hexahydro-1H-1,4-diazepino[1,2-a]indole, 1-oxo-2-benzyl-2,3,4,5,11,11a-hexahydro-1H-1,4-diazepino-[1,2-a]indole, hydrobromide, m.p. 210°, 1-oxo-2-(phenylethyl)-2,3,4,5,11,11a-hexahydro-1H-1,4-diazepino[1,2-a]indole and 1-oxo-2-p-methylbenzyl-2,3,4,5,11,11a-hexahydro-1H-1,4-diazepino[1,2-a]indole.

c. 2.3 g of 1-oxo-2,3,4,5,11,11a-hexahydro-1H-1,4-diazepino[1,2-a]indole are added in portions, while stirring, to a suspension of 1.7 g of LiAlH$_4$ in 60 ml of absolute THF and the mixture is then boiled for 10 hours. After cooling, 10 ml of 5% sodium hydroxide solution are added, the mixture is filtered and the filtrate is evaporated. The residue is dissolved in 20 ml of dilute hydrochloric acid, which is washed with ether, and the aqueous phase is made alkaline and extracted several times with ether. After drying and evaporation, 2,3,4,5,11,11a-hexahydro-1H-1,4-diazepino-[1,2-a]indole, hydrochloride, m.p. 234°, is obtained.

The corresponding hexahydro-diazepino-indoles, for example, 8-chloro-2,3,4,5,11,11a-hexahydro-1H-1,4-diazepino-[1,2-a]indole, hydrochloride, m.p. 226°, are obtained analogously from the corresponding 1-oxo compounds.

The corresponding 2-alkyl derivatives are obtained analogously from the corresponding 2-acyl compounds described in Example 1c), for example the corresponding 2-ethyl derivative (hydrochloride, m.p. 204°) or 2-(3-dimethylaminopropyl) derivative (dihydrobromide, m.p. 261°) is obtained from 2-acetyl- or 2-(3-dimethylaminopropionyl)-2,3,4,5,11,11a-hexahydro-1H-1,4-diazepino[1,2-a]indole.

EXAMPLE 3

A mixture of 2.93 g of 1-phenyl-2-bromomethyl--ethyl-hexahydro-diazepine -ethyl-hexahydro-bidazpine (obtainable from 1-phenyl-2-hydroxymethyl-4-ethyl-hexahydro-diazepine and POBr$_3$) and 2.9 g of AlCl$_3$ in 50 ml of petroleum ether (boiling point 60° – 80°) is stirred for an hour at 20° and is then boiled for three hours. After decomposition with ice water, the mixture is worked up in the customary manner with ether. This gives 2-ethyl-2,3,4,5,11,11a-hexahydro-1H-1,4-diazepino[1,2-a]indole, dihydrochloride, m.p. 204°.

EXAMPLE 4

A mixture of 2.34 g of 1-phenyl-2-hydroxymethyl-4-ethyl-hexahydro-diazepine (obtainable by an addition reaction of 2,3-dibromopropanol with N-ethylaminopropylaniline) and 80 g of polyphosphoric acid is stirred at 160° for an hour. After cooling, the mixture is decomposed with ice water, made alkaline and worked up in the customary manner with ether. This gives 2-ethyl-2,3,4,5,11,11a-hexahydro-1H-1,4-diazepino[1,2-a]indole, dihydrochloride, m.p. 204°.

EXAMPLE 5

34 ml of a 0.9 M solution of phenyllithium in ether are added, under nitrogen and over the course of an hour, to a boiling solution of 2.53 g of 1-ethyl-3-m-chlorobenzyl-hexahydro-diazepine (obtainable by reacting 1,2-dibromo-3-m-chlorophenyl-propane with 1-amino-3-ethylaminopropane) and 2 g of diethylamine in 250 ml of ether. After boiling for a further two hours, the mixture is hydrolysed with dilute hydrochloric acid and worked up in the customary manner. This gives 2-ethyl-2,3,4,5,11,11a-hexahydro-1H-1,4-diazepino[1,2-a]indole, dihydrochloride, m.p. 204°.

The same product is obtained analogously from 1-ethyl-3-o-bromobenzyl-hexahydro-diazepine.

EXAMPLE 6

2.78 g of iron-II sulphate are added in portions, at −5°, to a solution of 2.53 g of 1-chloro-2-benzyl-4-ethyl-hexahydro-diazepine (obtainable from 2-benzyl-4-ethyl-hexahydro-diazepine and sodium hypochlorite) in 10 ml of sulphuric acid and the mixture is stirred for an hour. After the customary working up with water/ether, 2-ethyl-2,3,4,5,11,11a-hexahydro-1H-1,4-diazepino[1,2-a]indole, hydrochloride, m.p. 204° is obtained.

EXAMPLE 7 a. A solution of 2.97 g of 2-(N-3-bromopropyl-N-methyl-carbamoyl)-indoline [obtainable by reacting indoline-2-carboxylic acid methyl ester with N-3-hydroxypropyl-N-methylamine and reacting the resulting 2-(N-3-hydroxypropyl-N-methyl-carbamoyl)-indoline with PBr$_3$] in 80 ml of ethylene glycol monomethyl ether is boiled for 20 hours with 0.75 g of potassium carbonate. The mixture is then worked up in the customary manner with water and ethyl acetate. This gives 1-oxo-2-methyl-2,3,4,5,11,11a-hexahydro-1H-1,4-diazepino-[1,2-a]indole. Hydrobromide, m.p. 241°.

The following compounds are obtained analogously by cyclizing the correspondingly substituted indolines:

1-Oxo-2-methyl-7-fluoro-2,3,4,5,11,11a-hexahydro-1H-1,4-diazepino[1,2-a]indole,
1-oxo-2-methyl-8-fluoro-2,3,4,5,11,11a-hexahydro-1H-1,4-diazepino[1,2-a]indole,
1-oxo-2-methyl-9-fluoro-2,3,4,5,11,11a-hexahydro-1H-1,4-diazepino[1,2-a]indole,
1-oxo-2-methyl-10-fluoro-2,3,4,5,11,11a-hexahydro-1H-1,4-diazepino[1,2-a]indole,
1-oxo-2-methyl-7-chloro-2,3,4,5,11,11a-hexahydro-1H-1,4-diazepino[1,2-a]indole,
1-oxo-2-methyl-8-chloro-2,3,4,5,11,11a-hexahydro-1H-1,4-diazepino[1,2-a]indole,
1-oxo-2-methyl-9-chloro-2,3,4,5,11,11a-hexahydro-1H-1,4-diazepino[1,2-a]indole,
1-oxo-2-methyl-10-chloro-2,3,4,5,11,11a-hexahydro-1H-1,4-diazepino[1,2-a]indole,
1-oxo-2-methyl-7-trifluoromethyl-2,3,4,5,11,11a-hexahydro-1H-1,4-diazepino[1,2-a]indole,
1-oxo-2-methyl-8-trifluoromethyl-2,3,4,5,11,11a-hexahydro-1H-1,4-diazepino[1,2-a]indole,
1-oxo-2-methyl-9-trifluoromethyl-2,3,4,5,11,11a-hexahydro-1H-1,4-diazepino[1,2-a]indole,
1-oxo-2-methyl-10-trifluoromethyl-2,3,4,5,11,11a-hexahydro-1H-1,4-diazepino[1,2-a]indole,
1-oxo-2,7-dimethyl-2,3,4,5,11,11a-hexahydro-1H-1,4-diazepino[1,2-a]indole,
1-oxo-2,8-dimethyl-2,3,4,5,11,11a-hexahydro-1H-1,4-diazepino[1,2-a]indole,
1-oxo-2,9-dimethyl-2,3,4,5,11,11a-hexahydro-1H-1,4-diazepino[1,2-a]indole,
1-oxo-2,10-dimethyl-2,3,4,5,11,11a-hexahydro-1H-1,4-diazepino[1,2-a]indole,
1-oxo-2-methyl-7-methoxy-2,3,4,5,11,11a-hexahydro1H-1,4-diazepino[1,2-a]indole,
1-oxo-2-methyl-8-methoxy-2,3,4,5,11,11a-hexahydro-1H-1,4-diazepino[1,2-a]indole,
1-oxo-2-methyl-9-methoxy-2,3,4,5,11,11a-hexahydro-1H-1,4-diazepino[1,2-a]indole,
1-oxo-2-methyl-10-methoxy-2,3,4,5,11,11a-hexahydro-1H-1,4-diazepino[1,2-a]indole,
1-oxo-2-ethyl-7-fluoro-2,3,4,5,11,11a-hexahydro-1H-1,4-diazepino[1,2-a]indole,
1-oxo-2-ethyl-8-fluoro-2,3,4,5,11,11a-hexahydro-1H-1,4-diazepino[1,2-a]indole,
1-oxo-1-ethyl-9-fluoro-2,3,4,5,11,11a-hexahydro-1H-1,4-diazepino[1,2-a]indole,
1-oxo-2-ethyl-10-fluoro-2,3,4,5,11,11a-hexahydro-1H-1,4-diazepino[1,2-a]9 indole,
1-oxo-2-ethyl-7-chloro-2,3,4,5,11,11a-hexahydro-1H-1,4-diazepino[1,2-a]indole,
1-oxo-2-ethyl-8-chloro-2,3,4,5,11,11a-hexahydro-1H-1,4-diazepino[1,2-a]indole,
1-oxo-2-ethyl-9-chloro-2,3,4,5,11,11a-hexahydro-1H-1,4-diazepino[1,2-a]indole,
1-oxo-2-ethyl-10-chloro-2,3,4,5,11,11a-hexahydro-1H-1,4-diazepino[1,2-a]indole,
1-oxo-2-ethyl-7-trifluoromethyl-2,3,4,5,11,11a-hexahydro1H-1,4-diazepino[1,2-a]indole,
1-oxo-2-ethyl-8-trifluoromethyl-2,3,4,5,11,11a-hexahydro-1H-1,4-diazepino[1,2-a]indole,
1-oxo-2-ethyl-9-trifluoromethyl-2,3,4,5,11,11a-hexahydro-1H-1,4-diazepino[1,2-a]indole,
1-oxo-2-ethyl-10-trifluoromethyl-2,3,4,5,11,11a-hexahydro-1H-1,4-diazepino[1,2-a]indole,
1-oxo-2-ethyl-7-methyl-2,3,4,5,11,11a-hexahydro-1H-1,4-diazepino[1,2-a]indole,
1-oxo-2-ethyl-8-methyl-2,3,4,5,11,11a-hexahydro1H-1,4-diazepino[1,2-a]indole,
1-oxo-2-ethyl-9-methyl-2,3,4,5,11,11a-hexahydro-1H-1,4-diazepino[1,2-a]indole, hydrobromide, m.p. 234°,
1-oxo-2-ethyl-10-methyl-2,3,4,5,11,11a-hexahydro-1H-1,4-diazepino[1,2-a]indole,
1-oxo-2-ethyl-7-methoxy-2,3,4,5,11,11a-hexahydro-1H1,4-diazepino[1,2indole,
1-oxo-2-ethyl-8-methoxy-2,3,4,5,11,11a-hexahydro-1H-1,4-diazepino[1,2-a]indole,
1-oxo-2-ethyl-9-methoxy-2,3,4,5,11,11a-hexahydro-1h-1,4-diazepino[1,2-a]indole and
1-oxo-2-ethyl-10-methoxy-2,3,4,5,11,11a-hexahydro-1H-1,4,-diazepino[1,2-a]indole.

b. Analogously to Example 2c), 2-methyl-2,3,4,5,11,11a-hexahydro-1H-1,4-diazepino[i,2-a]indole is obtained from 1-oxo-2-methyl-2,3,4,5,11,11a-hexahydro-1H-1,4-diazepino-[1,2-a]indole, using LiAlH$_4$.

The following compounds are obtained analogously from the corresponding lactams, using LiAlH$_4$:

2-Methyl-7-flouro-2,3,4,5,11,11a-hexahydro-1H-1,4-diazepino-[1,2-a]indole,
2-methyl-8-flouro-2,3,4,5,11,11a-hexahydro-1H-1,4-diazepino-[1,2-a]indole,
2-methyl-9-fluoro-2,3,4,5,11,11a-hexahydro-1H-1,4-diazepino-[1,2-a]indole, 2-methyl-10-flouro-2,3,4,5,11,11a-hexahydro-1H-1,4-diazepino-[1,2-a]indole,
2-methyl-7-chloro-2,3,4,5,11,11a-hexahydro-1H-1,4-diazepino-[1,2-a]indole,
2-methyl-8-chloro-2,3,4,5,11,11a-hexahydro-1H-1,4-diazepino-[1,2-a]indole,
2-methyl-9-chloro-2,3,4,5,11,11a-hexahydro-1H-1,4-diazepino-[1,2-a]indole, hydrochloride, m.p. 237°,
2-methyl-10-chloro-2,3,4,5,11,11a-hexahydro-1H-1,4-diazepino-[1,2-a]indole,
2-methyl-7-trifluoromethyl-2,3,4,5,11,11a-hexahydro-1H-1,4-diazepino[1,2-a]indole,
2-methyl-8-trifluoromethyl-2,3,4,5,11,11a-hexahydro-1H-1,4-diazepino[1,2-a]indole,
2-methyl-9-trifluoro-methyl-2,3,4,5,11,11-a-hexahydro-1H-1,4-diazepino[1,2-a]indole,
2-methyl-10-trifluoromethyl-2,3,4,5,11,11a-hexahydro-1H-1,4-diazepino[1,2-a]indole,
2,7-dimethyl-2,3,4,5,11,11a-hexahydro-1H-1,4-diazepino-[1,2-a]indole,
2,7-dimethyl-2,3,4,5,11,11a-hexahydro-1H-1,4-diazepino-[1,2-a]indole,
2,8-dimethyl-2,3,4,5,11,11a-hexahydro-1H-1,4-diazepino-[1,2-a]indole,
2,9-dimethyl-2,3,4,5,11,11a-hexahydro-1H-1,4-diazepino-[1,2-a]indole,
2,10-dimethyl-2,3,4,5,11,11a-hexahydro-1H-1,4-diazepino-[1,2-a]indole,
2-methyl-7-methoxy-2,3,4,5,11,11a-hexahydro-1H-1,4-diazepino-[1,2-a]indole,
2-methyl-8-methoxy-2,3,4,5,11,11a-hexahydro-1H-1,4-diazepino-[1,2-a]indole,
2-methyl-9-methoxy-2,3,4,5,11,11a-hexahydro-1H1,4-diazepino-[1,2-a]indole,
2-methyl-10-methoxy-2,3,4,5,11,11a-hexahydro-1H-1,4-diazepino[1,2-a]indole,
2-ethyl-7-flouro-2,3,4,5,11,11a-hexahydro-1H-1,4-diazepino-[1,2-a]indole,
2-ethyl-8-flouro-2,3,4,5,11,11a-hexahydro-1H-1,4-diazepino-[1,2-a]indole,
2-ethyl-9-fluoro-2,3,4,5,11,11a-hexahydro-1H-1,4-diazepino-[1,2-a]indole,
2-ethyl-10-fluoro-2,3,4,5,11,11a-hexahydro-1H-1,4-diazepino-[1,2-a]indole.
2-ethyl-7-chloro-2,3,4,5,11,11a-hexahydro-1H-1,4-diazepino-[1,2-a]indole,
2-ethyl-8-chloro-2,3,4,5,11,11a-hexahydro-1H-1,4-diazepino-[1,2-a]indole, hydrochloride, m.p. 195°,
2-ethyl-9-chloro-2,3,4,5,11,11a-hexahydro-1H-1,4-diazepino[1,2-a]indole,
2-ethyl-10-chloro-2,3,4,5,11,11a-hexahydro-1H-1,4-diazepino-[1,2-a]indole,
2-ethyl-7-trifluoromethyl-2,3,4,5,11,11a-hexahydro-1H-1,4-diazepino[1,2-a]indole,
2-ethyl-8-trifluoromethyl-2,3,4,5,11,11a-hexahydro-1H-1,4-diazepino[1,2-a]indole,
2-ethyl-9-trifluoromethyl-2,3,4,5,11,11a-hexahydro-1H-1,4-diazepino[1,2-a]indole,
2-ethyl-10-trifluoromethyl-2,3,4,5,11,11a-hexahydro1H-1,4-diazepino[1,2]indole,
2-ethyl-7-methyl-2,3,4,5,11,11a-hexahydro-1H-1,4-diazepino-[1,2-a]indole,
2-ethyl-8-methyl-2,3,4,5,11,11a-hexahydro-1H-1,4-diazepino-[1,2-a]indole,
2-ethyl-9-methyl-2,3,4,5,11,11a-hexahydro-1H-1,4-diazepino-[1,2-a]indole, hydrochloride, m.p. 226°,
2-ethyl-10-methyl-2,3,4,5,11,11a-hexahydro-1H-1,4-diazepino-[1,2-a]indole,
2-ethyl-7-methoxy-2,3,4,5,11,11a-hexahydro-1H-1,4-diazepino-[1,2-a]indole,
2-ethyl-8-methoxy-2,3,4,5,11,11a-hexahydro-1H-1,4-diazepino-[1,2-a]indole,
2-ethyl-9-methoxy-2,3,4,5,11,11a-hexahydro-1H-1,4-diazepino-[1,2-a]indole and
2-ethyl-10-methoxy2,3,4,5,11,11a-hexahydro-1H-1,4-diazepino[1,2-a]indole.

EXAMPLE 8 a. A mixture of 2.44 g of 1-(3-chloropropyl)-2-chloromethyl-indoline, 3.2 g of benzylamine, 30 ml of acetone and 20 ml of water is boiled for 10 hours. 1-(3-Benzylaminopropyl)-2-chloromethyl-indoline and 1-(3-chloro-propyl)-2-benzylaminomethyl-indoline are formed intermediately and are not isolated. After the customary working up, 2-benzyl-2,3,4,5,11,11a-hexahydro-1H-1,4-diazepino-[1,2-a]indole is obtained.

b. 2.78 g of 2-benzyl-2,3,4,5,11,11a-hexahydro-1H-1,4-diazepino[1,2-a]indole in 35 ml of methanol are hydrogenated, at 20° and normal pressure, with 1 g of 5% Pd/C, and the mixture is filtered and evaporated to give 2,3,4,5,11,11a-hexahydro-1H-1,4-diazepino[1,2-a]indole. Hydrochloride, m.p. 234°.

EXAMPLE 9

A solution of 18.4 g of 2,3,4,5,-tetrahydro-1H-1,4-diazepino[1,2-a]indole (m.p. 75°–77°) in 200 ml of acetic acid and 45 ml of 2N hydrochloric acid is hydrogenated, at 60° and normal pressure, with 13 g of 5% of palladium/barium sulphate. The mixture is cooled, filtered and evaporated to give 2,3,4,5,11,11a-hexahydro-1H-1,4-diazepino[1,2-a]indole. Hydrochloride, m.p. 234° (from ethanol).

EXAMPLE 10

2.3 g of 2-ethyl-3-oxo-2,3,4,5,11,11a-hexahydro-1H-1,4-diazepino[1,2-a]indole [obtainable by reacting 2-(N-ethyl-N-benzylaminomethyl)-indoline with acrylic acid to give the 1-(2-carboxyethyl) derivative, splitting off the benzyl group by hydrogenolysis and cyclising the resulting 1-(2-carboxyethyl)-2-ethylaminomethyl-indoline with NaOC₂H₅]are added in portions, while stirring, to a suspension of 2 g of LiAlH, in 70 ml of absolute THF, and the mixture is then boiled for 10 hours. The mixture is cooled and 12 ml of 5% sodium hydride solution is added and it is filtered and the filtrate is evaporated. The residue is worked up in the customary manner with aqueous hydrochloric acid and ether to give 2-ethyl-2,3,4,5,11,11a-hexahydro-1H-1,4-diazepino[1,2-a]indole, dihydrochloride, m.p. 204°.

EXAMPLE 11

Analogously to Example 10, 1,5-dioxo-2,3,4,5,11,11a-hexahydro-1H-1,4-diazepino[1,2-a]indole (obtainable by reacting indoline-2-carboxylic acid methyl ester with 3-amino-propionic acid) is reacted to give 2,3,4,5,11,11a-hexahydro-1H-1,4-diazepino[1,2-a]indole. Hydrochloride, m.p. 234°.

EXAMPLE 12

Analogously to Example 10, 3,5-dioxo-3,4,5,11,11a-hexahydro-1H-1,4-diazepino[1,2-a]indole (obtainable from 2-aminomethylindoline and malonyl chloride) is reacted to give 2,3,4,5,11,11a-hexahydro-1H-1,4-diazepino[1,2-a]indole. Hydrochloride, m.p. 234°.

EXAMPLE 13

Analogously to Example 10, 5-oxo-2,3,4,5,11,11a-hexahydro-1H-1,4-diazepino[1,2-a]indole (obtainable from 2-aminomethylindoline and acrylic acid) is reacted to give 2,3,4,5,11,11a-hexahydro-1H-1,4-diazepino[1,2-a]indole. Hydrochloride, m.p. 234°.

EXAMPLE 14

2.16 g of 1,3-dioxo-2,3,4,5,11,11a-hexahydro-1H-1,4-diazepino[1,2-a]indole (obtainable from indoline-1-propionic acid 2-carboxylic acid dimethyl ester and ammonia) are dissolved in 20 ml of THF, 20 ml of a 1-molar solution of diborane in THF are added and the mixture is stirred for two hours. The excess diborane is then decomposed with ethanol and the mixture is evaporated and worked up with aqueous hydrochloric acid and ether. This gives 2,3,4,5,11,11a-hexahydro-1H-1,4-diazepino[1,2-a]indole, hydrochloride, m.p. 234°.

The following examples illustrate pharmaceutical preparations containing an acid addition salt of a hexahydrodiazepino-indole derivative of general Formula I:

EXAMPLE A

Tablets

A mixture consisting of 20 kg of 2,3,4,5,11,11a-hexahydro-1H-1,4-diazepino]1,2-a]indole hydrochloride, 500 kg of lactose, 160 kg of maize starch, 10 kg of cellulose powder and 10 kg of magnesium stearate is pressed into tablets in the customary manner in such a way that each tablet contains 20 mg of the active compound.

EXAMPLE B

Dragees

Analogously to Example A, tablets are pressed which are subsequently coated in the customary manner with a coating consisting of sugar, wheat starch, talc and tragacanth.

Tablets and dragees which contain one or more of the remaining active compounds of Formula I or of their physiologically acceptable acid addition salts, can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A hexahydrodiazepinoindole of the formula

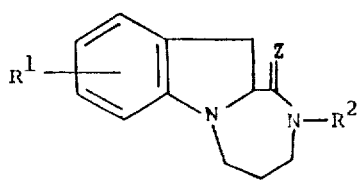

wherein $R^1$ is H, F, Cl, $CF_3$, alkyl or alkoxy each of 1 to 3 carbon atoms; $R^2$ is H, alkyl, cycloalkyl or alkenyl each of up to 6 carbon atoms, or alkyl of 1–6 carbon atoms substituted by one of oxo oxygen, (b) amino, alkylamino or dialkyl amino of 2 to 6 carbon atoms, (c) phenyl or alkyl phenyl of 6 to 8 carbon atoms, or (d) one each of two or three of (a), (b), and (c); and Z is O or (H,H), and physiologically acceptable acid addition salts thereof.

2. A compound of claim 1 wherein Z is (H,H).

3. A compound of claim 1 wherein $R^2$ is H, $CH_3$, $C_2H_5$, cyclopropyl, cyclohexyl, allyl, alkanoyl having 1 to 4 carbon atoms, 3-oxobutyl, 3-dimethyl-aminopropyl, dimethylaminoacetyl, benzyl or p-methylbenzyl.

4. A compound of claim 1, 2,3,4,5,11,11a-hexahydro-1H-1,4-diazepino[1,2-a]indole.

5. A compound of claim 1, 2-ethyl-2,3,4,5,11,11a-hexahydro-1H-1,4-diazepino[1,2-a]indole.

6. A compound of claim 1, 2-(3-oxobutyl)-2,3,4,5,11,11a-hexahydro-1H-1,4-diazepino[1,2-a]indole.

7. A compound of claim 1, 2-cyclopropyl-2,3,4,5,11,11a-hexahydro-1H-1,4-diazepino[1,2-a]indole.

8. A compound of claim 1, 2-allyl-2,3,4,5,11,11a-hexahydro-1H-1,4-diazepino[1,2-a]indole.

9. A compound of claim 1, 2-(3-dimethylaminopropyl)-2,3,4,5,11,11a-hexahydro-1H-1,4-diazepino[1,2-a]indole.

10. A compound of claim 1, 2-acetyl-2,3,4,5,11,11a-hexahydro-1H-1,4-diazepino[1,2-a]indole.

11. A compound of claim 1, 2-isobutyryl-2,3,4,5,11,11a-hexahydro-1H-1,4-diazepino[1,2-a]indole.

12. A compound of claim 1, 2-dimethylaminoacetyl-2,3,4,5,11,11a-hexahydro-1H-1,4-diazepino[1,2-a]indole.

13. A compound of claim 1, 9-methyl-2,3,4,5,11,11a-hexahydro-1H-1,4-diazepino[1,2-a]indole.

14. A compound of claim 1, 2-ethyl-9-methyl-2,3,4,5,11,11a-hexahydro-1H-1,4-diazepino[1,2-a]indole.

15. A compound of claim 1, 9-methoxy-2,3,4,5,11,11a-hexahydro-1H-1,4-diazepino[1,2-a]indole.

16. A compound of claim 1, 9-fluoro-2,3,4,5,11,11a-hexahydro-1H-1,4-diazepino[1,2-a]indole.

17. A compound of claim 1, 8-chloro-2,3,4,5,11,11a-hexahydro-1H-1,4-diazepino[1,2-a]indole.

18. A compound of claim 1, 9-chloro-2,3,4,5,11,11a-hexahydro-1H-1,4-diazepino[1,2-a]indole.

19. A compound of claim 1, 2-methyl-9-chloro-2,3,4,5,11,11a-hexahydro-1H-1,4-diazepino[1,2-a]indole.

20. A compound of claim 1, 2-(3-oxobutyl)-9-chloro-2,3,4,5,11,11a-hexahydro-1H-1,4-diazepino[1,2-a]indole.

21. A compound of claim 1, 2-(3-dimethylaminopropyl)-9-chloro-2,3,4,5,11,11a-hexahydro-1H-1,4-diazepino[1,2-a]indole.

22. A compound of claim 1, 10-chloro-2,3,4,5,11,11a-hexahydro-1H-1,4-diazepino[1,2-a]indole.

23. A compound of claim 1, 2-ethyl-10-chloro-2,3,4,5,11,11a-hexahydro-1H-1,4-diazepino[1,2-a]indole.

24. A compound of claim 1, 1-oxo-2,3,4,5,11,11a-hexahydro-1H-1,4-diazepino[1,2-a]indole.

25. A compound of claim 1, 1-oxo-2-methyl-2,3,4,5,11,11a-hexahydro-1H-1,4-diazepino[1,2-a]indole.

26. A compound of claim 1, 1-oxo-2-(3-dimethylaminopropyl)-2,3,4,5,11,11a-hexahydro-1H-1,4-diazepino[1,2-a]indole.

27. A compound of claim 1, 1-oxo-2-benzyl-2,3,4,5,11,11a-hexahydro-1H-1,4-diazepino[1,2-a]indole.

28. A compound of claim 1, 1-oxo-9-methyl-2,3,4,5,11,11a-hexahydro-1H-1,4-diazepino[1,2-a]indole.

29. A compound of claim 1, 1-oxo-2-ethyl-9-methyl-2,3,4,5,11,11a-hexahydro-1H-1,4-diazepino[1,2-a]indole.

30. A pharmaceutical composition adapted for oral ingestion comprising an amount from 1 to 500 mg. per dosage unit effective to induce a CNS-depressant effect of a compound of claim 1 in admixture with a pharmaceutically acceptable carrier.

31. A method for inducing a CNS-depressant effect in a mammal which comprises administering to a mammal a CNS-depressant effective amount of a compound of claim 1.

32. A compound of claim 1 wherein $R^2$ is H, alkyl or alkenyl each of up to 4 carbon atoms, cycloalkyl of 3 to 6 carbon atoms, alkanoyl of 1 to 4 carbon atoms, oxoalkyl of 3 or 4 carbon atoms, dialkylaminoalkyl or dialkylaminoaklanoyl each of a total of 4 to 7 carbon atoms, phenylalkyl or alkylphenylalkyl each of 7 to 10 carbon atoms.

* * * * *